United States Patent [19]
Baldwin

[11] Patent Number: 5,413,115
[45] Date of Patent: May 9, 1995

[54] BIOPSY SYRINGE WITH SLIDE VALVE

[76] Inventor: James R. Baldwin, 2200 W. Petty Rd., Muncie, Ind. 47304

[21] Appl. No.: 175,152

[22] Filed: Dec. 29, 1993

[51] Int. Cl.6 .................................................. A61B 5/00
[52] U.S. Cl. ..................................... 128/763; 123/766; 604/249
[58] Field of Search ............... 604/192, 198, 249, 403, 604/235, 236; 128/760, 763, 764, 765, 766

[56] References Cited

U.S. PATENT DOCUMENTS

| | | | |
|---|---|---|---|
| 1,015,276 | 1/1912 | Rowse . | |
| 3,143,109 | 8/1964 | Gewertz . | |
| 3,159,159 | 12/1964 | Cohen | 128/766 |
| 3,952,729 | 4/1976 | Libman et al. | 128/766 X |
| 4,073,288 | 2/1978 | Chapman . | |
| 4,267,846 | 5/1981 | Kontos | 128/765 |
| 4,423,741 | 1/1984 | Levy | 604/249 X |
| 4,427,015 | 1/1984 | Redeaux, Jr. . | |
| 4,542,749 | 9/1985 | Caselgrandi et al. | 128/763 X |
| 4,549,554 | 10/1985 | Markham . | |
| 4,619,272 | 10/1986 | Zambelli . | |
| 4,840,184 | 6/1989 | Garg | 128/763 X |
| 4,967,762 | 11/1990 | DeVries . | |
| 4,972,843 | 11/1990 | Broden | 128/760 |
| 4,986,278 | 1/1991 | Ravid . | |
| 5,184,652 | 2/1993 | Fan | 604/249 X |

*Primary Examiner*—Sam Rimell
*Attorney, Agent, or Firm*—Woodard, Emhardt, Naughton, Moriarty & McNett

[57] ABSTRACT

A pen-size syringe has a needle secured to a hub at one end and a valve located near the hub and slidable transversely of the syringe axis by the forefinger of the user, from a closed condition, to a sampling condition, to a needle venting condition. A plunger in the syringe is axially slidable by manually pulling a portion projecting out the other end of the syringe to establish a vacuum in the syringe when the valve is closed. A latch is provided to keep the plunger in the vacuum establishing position. With the vacuum established, and the needle point situated at the sampling site, the valve is operable by the index finger to open the vacuum chamber to the needle for taking the specimen, following which the finger pushes the valve to the further position venting to needle to atmosphere, for removal of the needle, and any contained sample.

10 Claims, 8 Drawing Sheets

5,413,115

BIOPSY SYRINGE WITH SLIDE VALVE

BACKGROUND OF THE INVENTION

1. Field of the Invention

This invention relates generally to-fine needle aspiration biopsy apparatus and methods, and more particularly to a syringe for use in such procedures.

2. Description of the Prior Art

There is a U.S. Pat. No. 4,549,554 issued Oct. 29, 1985 to Markham which discloses a syringe with a detachable valve 28 located at its end to regulate vacuum, and an opening 46 in the syringe body to vent the device after use. One embodiment shown in FIG. 4 of the patent shows a stop pin 114 inserted in a hole 112 in the piston to hold the withdrawn piston, to hold the vacuum until the specimen has been secured.

A U.S. Pat. No. 4,967,762 issued Nov. 6, 1990 to DeVries discloses a fine needle aspiration biopsy syringe which, although it does not have a valve for control of vacuum, shows an O-ring on the needle mounting attachment and which normally covers an opening 72 in the attachment (FIG. 2). When the sample has been drawn, the ring is rolled away from the opening to vent the vacuum, whereupon the needle can be withdrawn without disturbing the specimen.

U.S. Pat. No. 4,986,278 issued Jan. 22, 1991 to Ravid et al. discloses a two piston design for a biopsy syringe device, and which has a valve located near its end to regulate a vacuum. The vacuum is used to regulate the position of a needle.

U.S. Pat. No. 4,619,272 issued Oct. 28, 1986 to Zambelli discloses an instrument for performing biopsies and which includes a valve 24 which can be turned to open it and admit air into the suction chamber 10.

While the Markham and DeVries devices have some desirable functional features as mentioned above, greater simplicity and convenience of use is needed. The reason is the fact that, in fine needle aspiration biopsy procedures, it is desirable to be able to place and direct the needle with precision and to operate the vacuum control and vent easily. The necessity of using two hands or inconvenient or unnatural finger movements in order to secure a sample, can make a device inconvenient, awkward or difficult to use. It is an object of the present invention to provide a fine needle aspiration biopsy device that is easier to use.

SUMMARY OF THE INVENTION

Described briefly, according to a typical embodiment of the present invention, a syringe of the standard hypodermic syringe diameter of about 15 mm and 100 mm overall length (or conforming to dimensions typically seen in medical syringes of 3 cc to 30 cc capacity) includes a conventional needle hub at one end and a plunger operating handle or button at the other end. A stop is provided at the handle end to hold the plunger in a withdrawn position to establish and maintain vacuum in the vacuum chamber of the syringe while, at the other end, a variably positionable, finger operated slide valve is in a first position occluding the vacuum chamber to needle passageway. The valve is operable by the forefinger as the syringe is held by one hand in the manner of a pencil for movement from the occluding position to a vacuum communicating position and further, when desired, to a needle venting position.

DESCRIPTION OF THE PREFERRED EMBODIMENT

Figure 1:
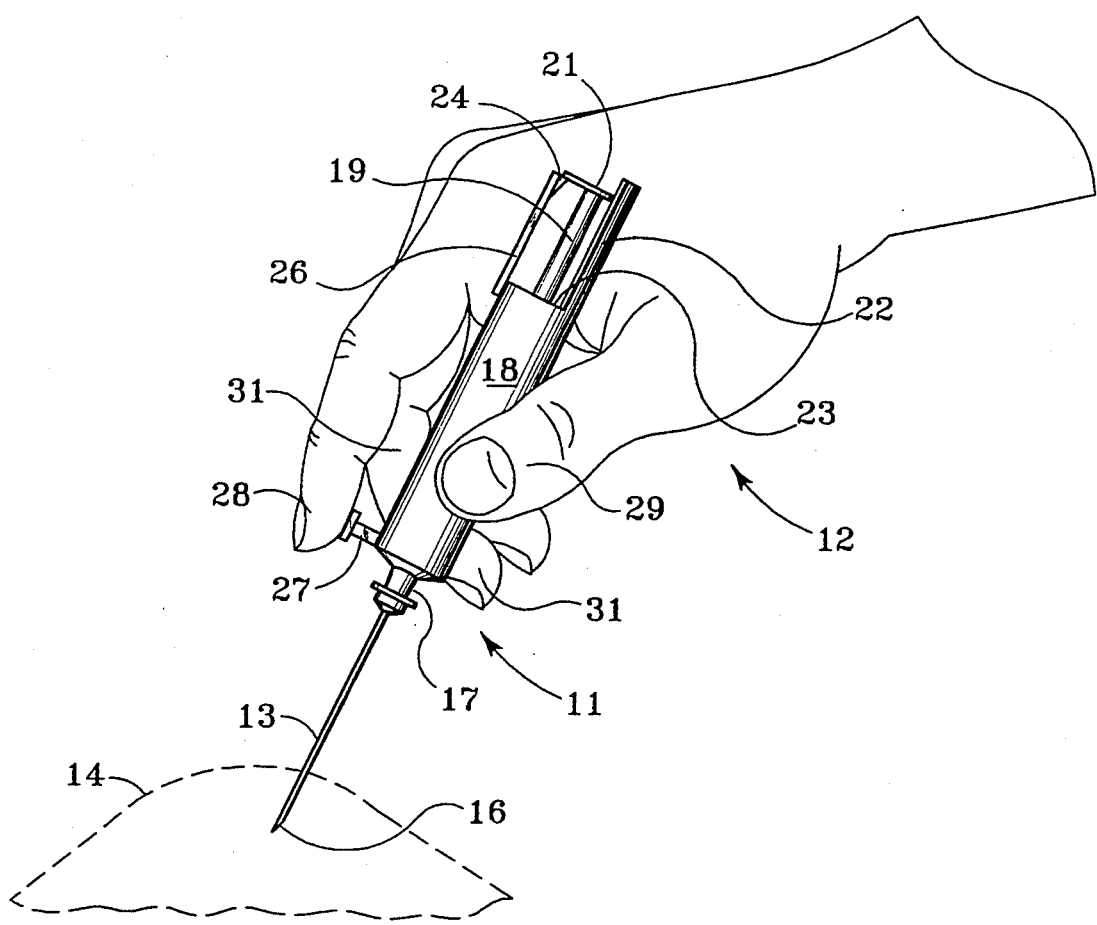
FIG. 1 is an elevational view showing the fine needle biopsy apparatus device according to a typical embodiment of the present invention and in-use.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, and particularly FIG. 1, the syringe assembly 11 is shown in the hand 12 of the physician with the needle 13 piercing the skin 14 of the subject and the hollow point 16 at the site from which the tissue sample is to be taken. The needle 13 is conventional and received on the hub 17 of the syringe. The syringe barrel 18 has a plunger or piston therein at the front end of the piston rod 19. A handle or flange 21 is secured at the rear end of the piston rod. A handle guide 22 affixed relative to and extending from the rear end 23 of the barrel 18 guides the handle flange 21. An abutment stop 24 is at the rear end of an arm 26 projecting from the rear of the barrel and fixed relative thereto.

A vacuum control valve slide 27 projects out of the top of the syringe barrel 18 near the hub end and is operable by the forefinger 28 of the hand 12 of the physician, while the barrel 18 is held between the thumb 29 and index finger 31 of the user's hand.

Figure 2:
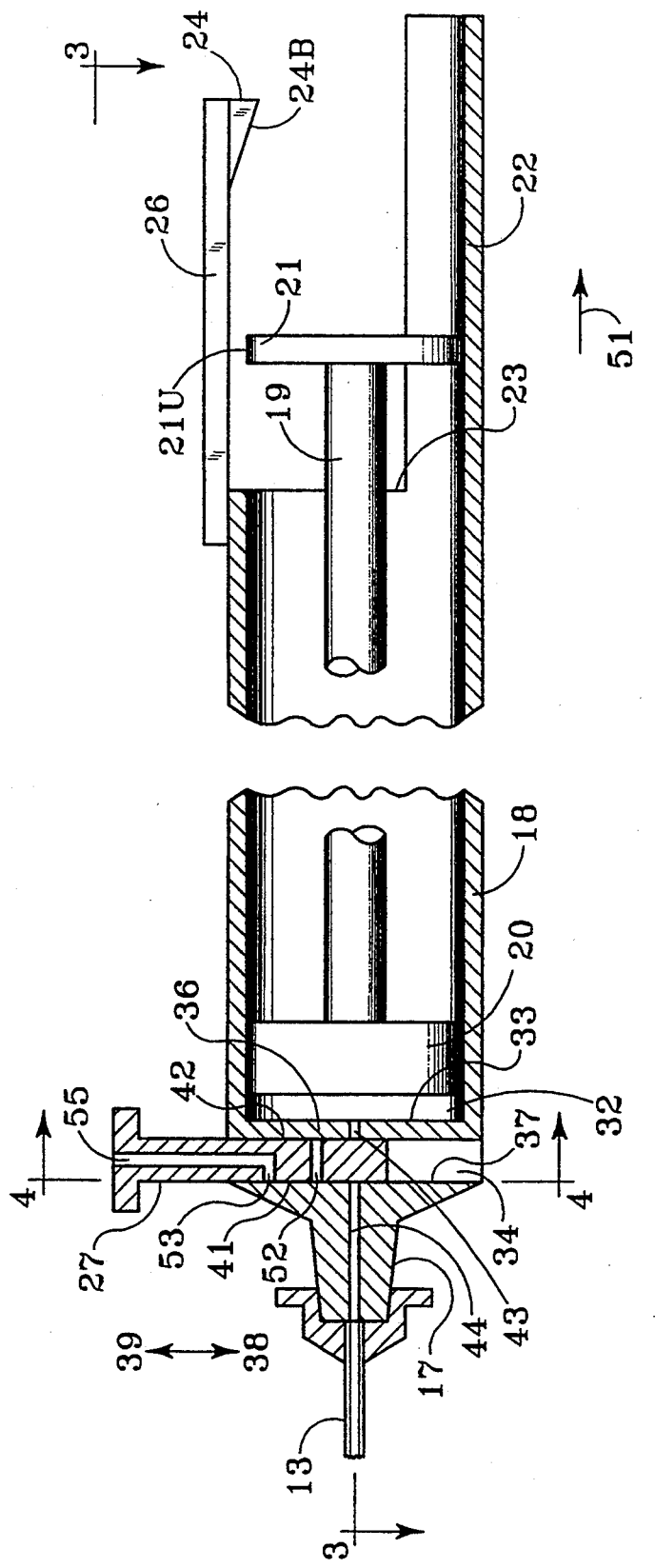
FIG. 2 is a longitudinal sectional view therethrough before use.

Referring now to FIGS. 2 and others, the plunger 20 is at the front end of the rod 19 and is slidably and fittingly received in the barrel 18 and shown in about its forwardmost position where the vacuum chamber 32 is at about its smallest volume. Typically the plunger would be near the barrel end wall 33 when the procedure starts.

Figure 3:
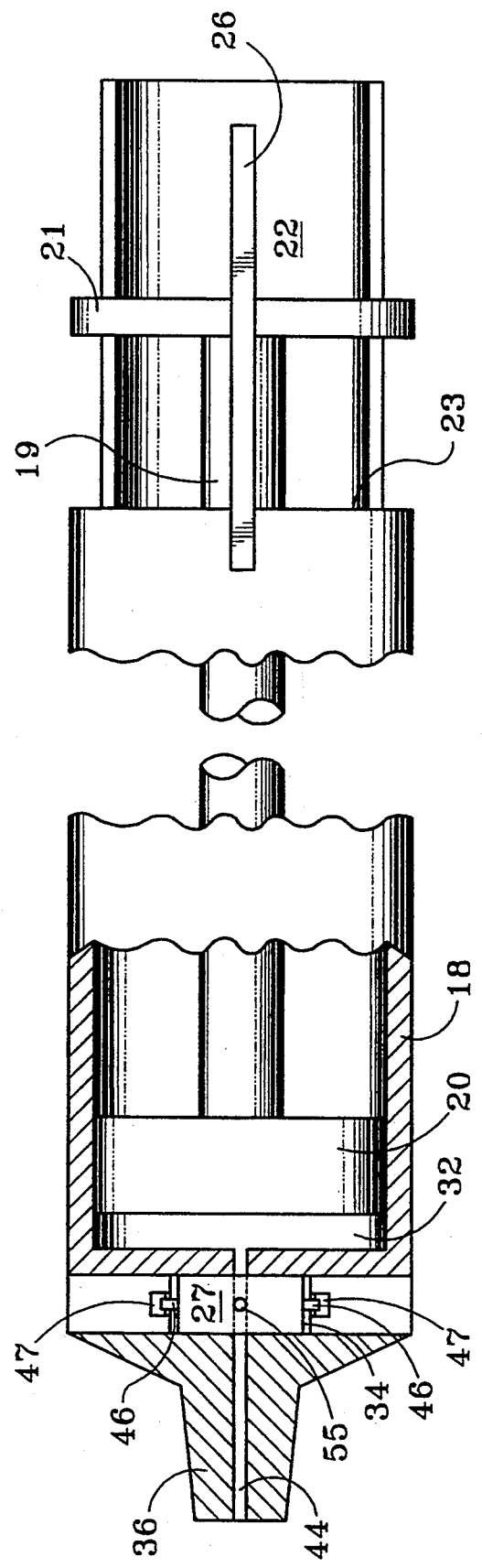
FIG. 3 is a section therethrough taken at line 3—3 in FIG. 2 and viewed in the direction of the arrows.
Figure 4:
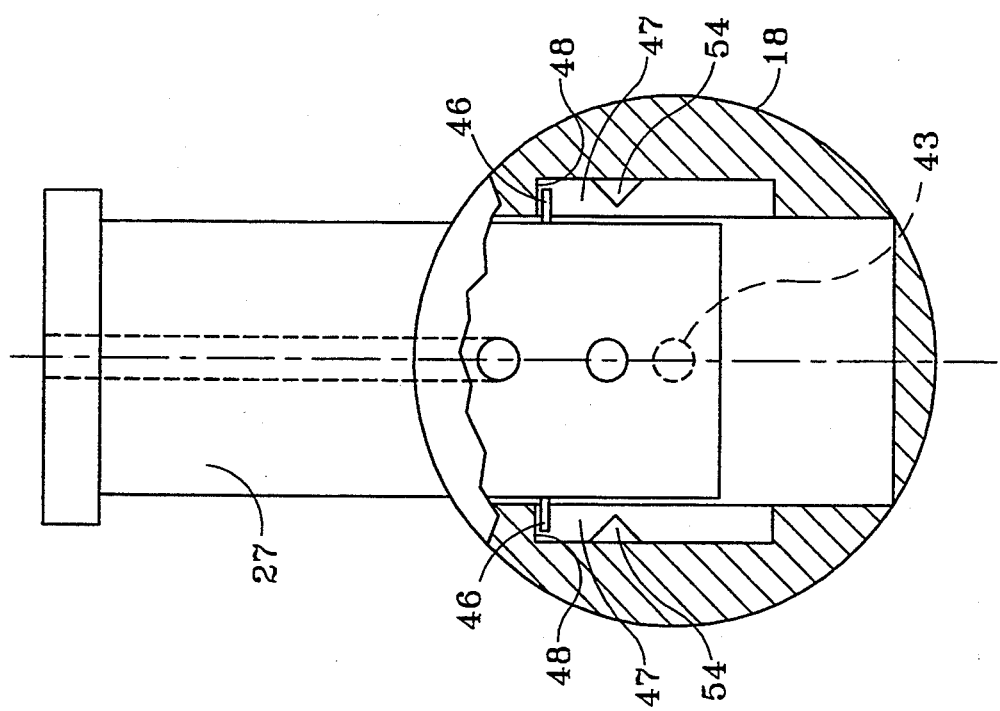
FIG. 4 is a section taken at line 4—4 in FIG. 2 and viewed in the direction of the arrows.

A slideway 34 which is rectangular in cross section as shown in FIG. 3, is provided near the front end of the barrel and fittingly receives the slide valve 27 therein at the front face 36 of the wall 33, and the rear face 37 of the front end portion of the barrel. Therefore, even though the slide valve can be moved in and out transverse to the axis of the cylinder in the direction of arrows 38 and 39, respectively, it is sealed at both the front and rear faces 41 and 42, respectively, against the front and rear faces 37 and 36 of the slideway. Therefore, when the slide valve 27 is in its uppermost position of FIGS. 2 and 4, it seals the aperture 43 in the center of the wall 33 and the aperture and passageway 44 in the center of the front end of the barrel. This valve has a couple of slightly flexible stop lugs 46 projecting laterally from it and received in grooves 47 in the front end of the barrel. The engagement of these lugs 46 with the upper walls 48 of the grooves 47 limits the upward travel of the slide valve. When in this condition, and as mentioned above, this valve occludes the two apertures 43 and 44. Therefore, when the valve is in this position, the operating handle or knob 21 at the end of the piston rod 19 can be pulled outward in the direction of arrow 51 in FIG. 2, thereby pulling the piston 20 outward and enlarging the vacuum chamber 32. As it does so, a vacuum is established in chamber 32 as the piston 20 snugly fits the bore of the barrel 18. The arm 26 is somewhat resilient so that, as the piston is pulled outward, the upper edge 21U of the handle flange 21 can slide under the cam surface 24B of the stop 24 and resiliently bend the arm 26 upward so that the rear end stop 24 will snap down in front of the flange 21 when the piston has been pulled back sufficiently to establish the desired vacuum in chamber 32.

Figure 5:
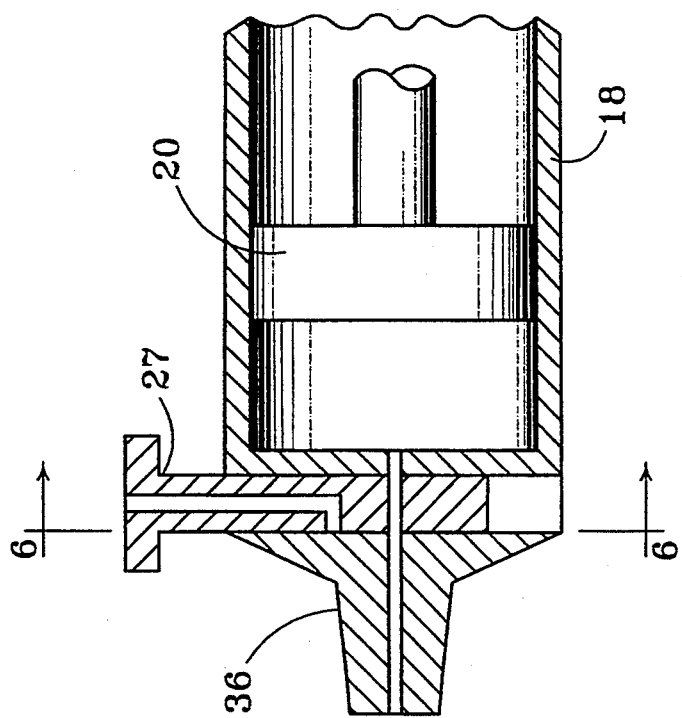
FIG. 5 is a sectional view of a portion of the device of FIG. 2 but showing the plunger retracted and vacuum chamber communicating with the needle.
Figure 6:
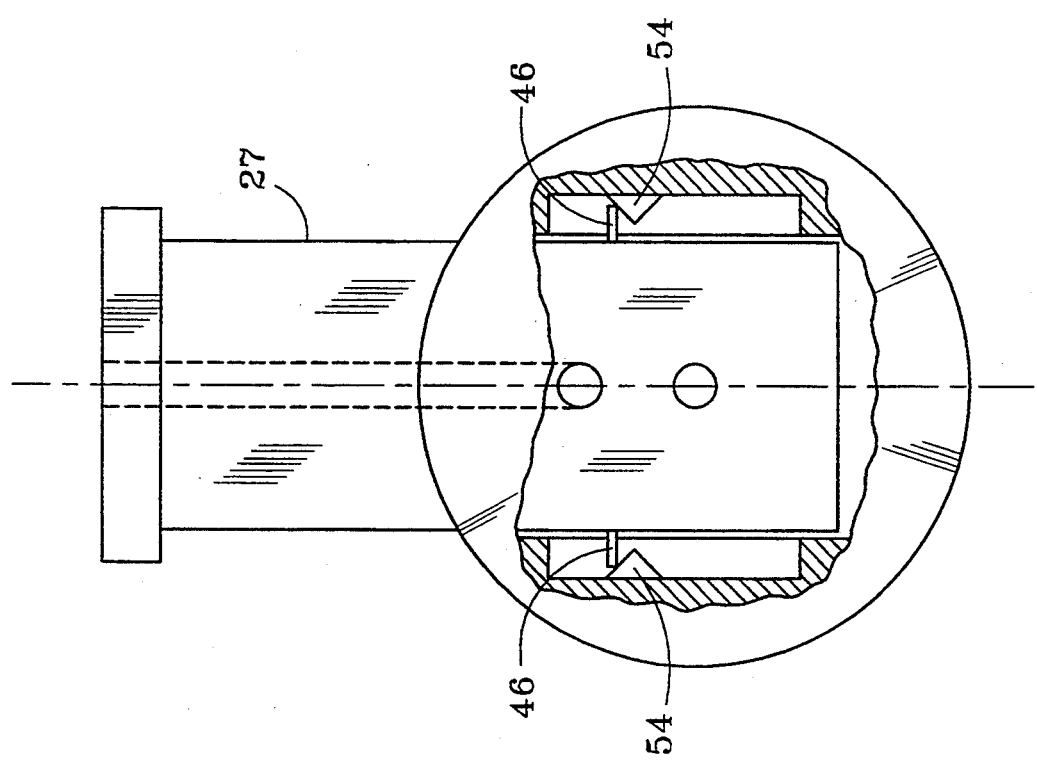
FIG. 6 is a section taken at line 6—6 in FIG. 5 and viewed in the direction of the arrows.
Figure 7:
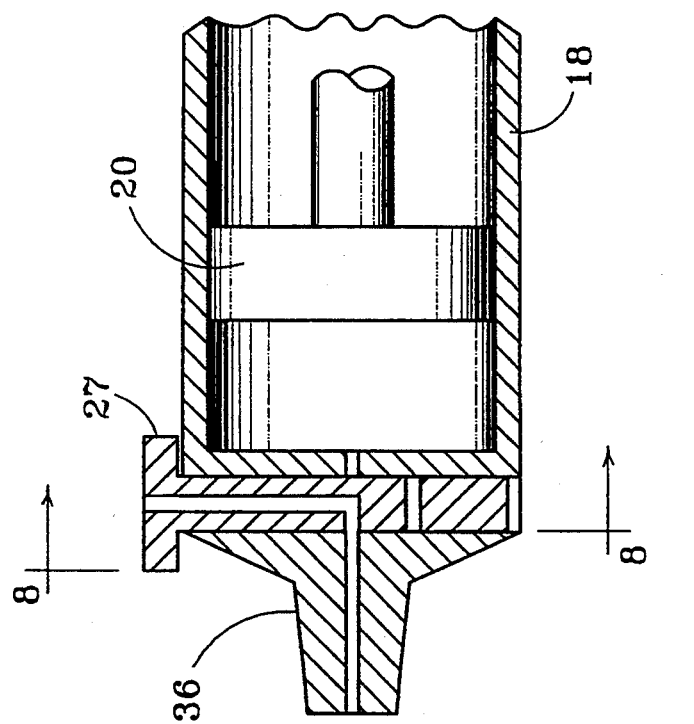
FIG. 7 is a view like FIG. 5 except showing the needle vented to atmosphere.

The valve 27 has two additional apertures 52 and 53 therein. Aperture 52 extends all the way through the valve from face 41 to face 42 so that, when valve 27 is pushed down by the finger 28 to the position shown in FIGS. 5 and 6, the aperture 52 is in registry with the passageways 43 and 44 providing communication from the needle through the front end of the barrel and the wall 33 into the vacuum chamber. Of course, this step of pushing the valve down to provide this condition is not performed until the needle end opening 16 is at the site from which the biopsy sample is to be taken, as shown in FIG. 1. To avoid over-travel of the valve beyond that point of registry of passageways 43, 44 and 52, there are angled stops 54 at the outside of each of the two grooves 47. These will be encountered by the lugs 46 as the valve is pushed downward and, unless excessive force is applied by the finger 28, the stops will stop the downward travel of the valve, whereupon the passageway 52 in the valve will be in registry with passageway 43 and 44.

After a sufficient amount of sample is take, and before the needle is removed from the biopsy site, the vacuum in the needle is terminated by pushing the valve 27 down farther for registry of passage 53 therein with the passageway 44, white the back wall of the valve occludes the passageway 43, thus sealing any specimen that may have accumulated in vacuum chamber 32. The lugs 46 are sufficiently flexible, and the ramp angles on the stops 54 are gentle enough that it does not take much pressure to push the valve from the second to this third position. Upon registry of passageway 53 in the valve with the passageway 44, air from the atmosphere can enter the "chimney" 55 in the slide valve, eliminating the vacuum from the needle, whereupon the needle can be withdrawn from the biopsy site. The needle is then removed and the material contained in its lumen is expressed onto a slide and smeared. In practice, some sample may accumulate in the vacuum chamber. To make smears of this material, the slide valve would be withdrawn to the second position and the plunger retaining latch released. This would allow the plunger to be repositioned near the barrel end wall 33, thereby expressing any material that may have accumulated in the chamber.

Figure 8:
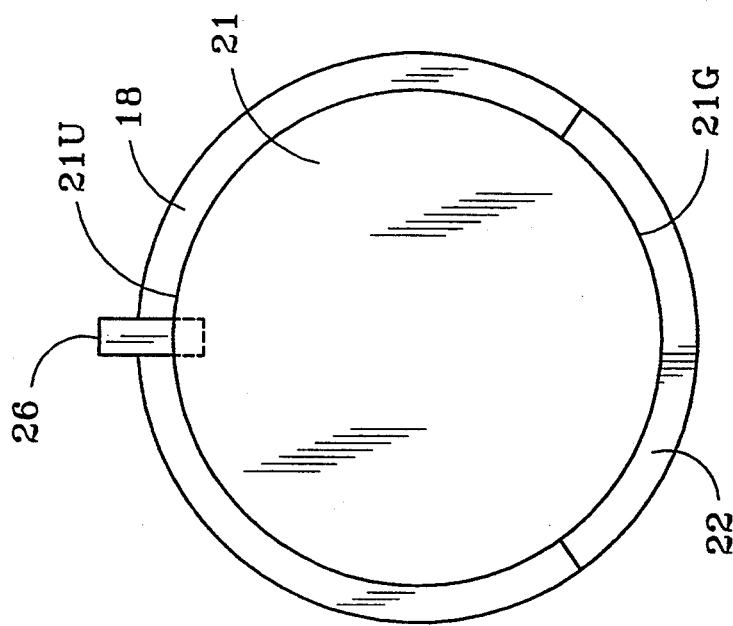
FIG. 8 is a rear elevational view.

While the piston 20 is shown without an elastomeric seal ring, and the rod 19 is shown as a solid cylinder, a ringed piston or a rod with a cross-shaped cross section, or other arrangements can be used. Also, while the rearward extension of the cylinder wall cradles and guides the plunger handle at 21G in FIG. 8 to help control and guide the handle 21 as it is pulled out, other arrangements might be used.

The size of the syringe can be chosen based on application. The diameter of the cylinder and plunger could be between 5 mm and 50 min. The piston travel could be 30 mm to 100 min.

The barrel may be of transparent thermoplastic material, as is true of all of the other components, except for the needle. Other materials might be used as well. The piston may be provided with rings or other means Co better seal against the barrel wall, if desired. Similarly, additional sealing features can be provided around the slideway end of passageway 43 or on the face 42 of the valve slide 27 to be sure that there is no leakage from atmosphere into the vacuum chamber. The needle to hub connection can be any suitable one of a variety known in the art.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A fine needle aspiration biopsy device comprising:
   a barrel;
   a needle mounting hub at the front end of the barrel;
   a needle mounted to the hub;
   a vacuum-establishing control member at the other end of the barrel;
   a valve in the barrel between the hub and the control member; and
   a latch on the barrel engageable with the control member to hold the control member in vacuum maintaining position;
   there being a first fluid passageway from the hub to the valve, and a second fluid passageway from the valve to a vacuum chamber in the barrel;
   the valve including a slideway between the hub and the control member, and the valve having a slide that is slidably received in the slideway, and the valve slide having third and fourth passageways therein, the valve slide having three positions, one of them placing the slide in a position occluding one of the first and second passageways thereby preventing communication from the first passageway to the second, another position placing the third passageway in registry with the first and second passageways thereby providing communication between the first passageway and the second passageway, and a third position placing the fourth passageway in registry with the first passageway and opening outside the body thereby providing communication between the first passageway and the environment around the device.

2. The device of claim 1 arid further comprising:
   a groove in the front end of the barrel and opening into the slideway;

at least one lug extending laterally from the slide into the groove; and at least one stop in the groove and engageable by the lug to impede passage of the lug as the slide is moved along the slideway.

3. The device of claim 2 and wherein:

the stop has angled faces engageable by the lug, and the lug is flexible to enable passage across the stop by resilient deformation of the lug during passage.

4. The device of claim 2 and wherein:

the stop is so located along the length of the slideway to define the second of the valve positions.

5. The device of claim 4 and wherein:

there is an abutment wall at one end of the groove and engageable by the lug and defining one of the valve positions.

6. The device of claim 5 and wherein:

the three positions are defined longitudinally of the slideway.

7. A fine needle aspiration biopsy device comprising:

a barrel having a diameter less than 50 mm;

a needle mounted at one end of the barrel;

a vacuum chamber in the barrel;

a slideway near the front end of the barrel;

a valve including a slide slidably received in the slideway and located between the needle and the vacuum chamber and operable in three positions;

the vacuum chamber having a front wall;

a first fluid passageway from the needle to the valve;

a second fluid passageway through the valve;

a third fluid passageway through the valve; and a fourth fluid passageway through the front wall of the vacuum chamber; whereby the valve when in the first of the three positions occludes an end of the fourth passageway;

the valve when in the second position places the second passageway in registry with the first and fourth passageways thereby providing communication between the needle and the vacuum chamber; and the valve when in the third position places the third passageway in communication with the first passageway and thereby vents the needle to the environment around the device;

the valve having an actuator projecting outward from the barrel near the needle mounting end of the barrel and operable by one finger of a hand while holding the barrel in the hand to move the valve from the first position to and then through the second position to the third position.

8. The device of claim 7 and further comprising:

cooperating stops on the slideway and the slide and operative to inhibit passage of the slide from one position through the next position.

9. The device of claim 7 and further comprising:

a plunger having a portion in the barrel and defining one wall of the vacuum chamber, the plunger being sealed in the barrel but slidable longitudinally in the barrel; and a latch on the barrel and engageable with a portion of the barrel to retain the plunger in a vacuum maintaining position of the wall of the chamber.

10. The device of claim 7 and wherein:

the valve has a front wall and a rear wall, the second passageway extends through the valve from the front wall to the rear wall, and the third passageway extends in the valve from the front wall toward the rear wall but then turns, whereby the rear wall of the valve behind the third passageway is closed and occludes the fourth passageway when the valve is in the third position.

* * * * *